US005907083A

United States Patent [19]

Robert et al.

[11] Patent Number: 5,907,083

[45] Date of Patent: May 25, 1999

[54] BRASSICA SP. GENE PROMOTER HIGHLY EXPRESSED DURING STIGMA DEVELOPMENT

[75] Inventors: Laurian Robert, Gatineau; Jean L. Gerster, Ottawa; John Simmonds, Nepean, all of Canada

[73] Assignee: Her Majesty the Queen in right of Canada as represented by Agriculture and Agri-Food Canada, Canada

[21] Appl. No.: 08/617,101

[22] Filed: Mar. 18, 1996

[51] Int. Cl.[6] .......................... C12N 15/29; C12N 15/82; A01H 4/00; A01H 5/00

[52] U.S. Cl. .................................. 800/205; 800/DIG. 15; 536/23.6; 536/24.1; 435/172.3; 435/320.1

[58] Field of Search ................................. 536/24.1, 23.6; 435/172.3, 320.1; 800/205, DIG. 15

[56] References Cited

FOREIGN PATENT DOCUMENTS

PCT/US94/04557 5/1994 WIPO ............................ C12N 15/82

OTHER PUBLICATIONS

Roger Lewin. When does homology mean something else? Science. vol. 237, 1570, Sep. 1987.

Reeck et al. "Homology" in proteins and nucleic acids: A terminology muddle and a way out of it. Cell. vol. 50, 667, Aug. 1987.

Thorsness et al. A Brassica S–locus gene promoter targets toxic gene expression and cell death to the pistil and pollen of transgenic Nicotiana. Developmental Biology 143: 173–184 (1991).

Robert et al. Molecular analysis of two Brassica napus genes expressed in the stigma. Plant Molecular Biology 26: 1217–1222, 1994.

Hackett, R.M. et al. (1992). "A *Brassica* S–locus related gene promoter directs expression in both pollen and pistil of tobacco", *The Plant Journal* 2:613–617.

Dzelzkalns, V.A. et al. (1993). "Distinct *cis*–Acting Elements Direct Pistil–Specific and Pollen–Specific Activity of the Brassica S Locus Glycoprotein Gene Promoter", *The Plant Cell* 5:855–863.

Goldman, M.H.S. et al. (1994). "Female sterile tobacco plants are produced by stigma–specific cell ablation", *The EMBO Journal* 13:2976–2984.

"Molecular Analysis of two *Brassica Napus* genes expressed in the stigma" Laurian S. Robert, et al., *Plant Molecular Biology*, 26:1217–1222, 1994.

*Primary Examiner*—Douglas W. Robinson
*Assistant Examiner*—Thomas Haas
*Attorney, Agent, or Firm*—Rothwell, Figg, Ernst & Kurz, P.C.

[57] ABSTRACT

A Brassica sp. genomic clone G 363 containing a gene promoter, which directs expression in the stigma, was isolated. Based on microbombardment studies of *Brassica napus* flowers with the gene Pis 63/Gus fusion, the Pis 63 promoter was shown to direct GUS expression to the stigma. This promoter will be useful for the temporal and spatial control of gene expression in plants.

15 Claims, 4 Drawing Sheets

```
                10         20         30         40         50         60
                 |          |          |          |          |          |
   1 GGGGATCTAT CTTAGATATT GTTTGAAAAG AGAGTACCAA CTCTCCCATA CTCAAAGTCA

  61 CAGAAGTCAA ATGTTGTTTG AAATAATTAT AGCATTTGTT TGTTTTAGTT AAAAGTTTGA

 121 AAAACTACGA ACGATTTATG GATCATCATT CATCACGCAT ATTGTTAATG TGAGAACCAG

 181 ACCAATAGTT TCTTAAGTAT TGAATATACA AAAAACATTT GATAAACAAA TCTTTCGCTT

 241 TGGAAAAATA TAGGGTGGGT AATATTTTGT ATAATCTAAG CGGCTTGTTC ATTTGTAATC

 301 ATGGATTTTA ATGTTTTTGA TGACTTTGTT TGTGGATGTG CAACTGCATA TTTTTAGTTT

 361 TTTTTGTTTG TTAATTGTGT TGTGATCCTT AATCCTAATT ATGAAACACA CAAGTATGAC

 421 TGATAAGAGT TAGTAAGCAT TCGGTGGTCA AGATATTTAG TGGCTAGCGA CCTACCCCTA

 481 ATTTATTTAT TTATTTTAAC TAATCTTTAT TTGATCGTTC ATTATGTCAA CAAACTTTCT

 541 TCTTCTCTAA AGTACGTGAA ATTACTACTA CATTTTAATA CTGCAATTGA AGTAAGTAGT

 601 ACGGTTTTCA TCTCTTAAAT GCATGGAAAC AAACACTAAT ACGTAGCAAA ATTGAGAGAA

 661 CATATACTAT GCTTCGCACC GGATTTTATT AGAGCATTTG ACACACTAAA GTCCCACATG

 721 GTTACCAGCA GGGCCTGCCC TGAGATTTAG AGGGAGGTGG TTTTTAAAAA AAATTCCGTT

 781 AAAAATTTTT TTTGGTAAAT TTGGAGGTCT AAAAAAAAAT TTTAAAAGTT TTTTCCTATG

 841 TAATTTTTTC CAAAATTTTT AGAGGTCTAA GCCTAATATT TCGTTAGGCT TTAAGCAGGA

 901 CCGGCCCTGG TTACCATATG TATAATACAT ACACAAAACA CAATTGTGTT GTCGTTTTTA

 961 GTACTTTGTG TCCGTTTCAT TGTATATGAC GTACGTAACC ATTCAAAACC TAATTAAATA

1021 TGGTGATCCC CTAATTGATC ACATTCTAAG CTCTGGTAAA CTTCTCATGG CATACTCTTT
```

FIGURE 1

```
1081 TGATTTCGTA AACCCTTTCT CAAAAAGCTA TTTTCGTATT AATTTGGTAA GAATTATTTT
1141 CCTGGTCCAT GTAGGTTTTG TATGTTTTTT TTTTTGATAA CTCTGGTATC TGGGCAGCCA
1201 CATTCCCAAC TATCCATTCG AAAGGGGTCC AGCGCCCCGG GATGTTAAAT CCTGTTGTGG
1261 CCAAGGCTCG AACCCGGGTA GCGGCAGTAC AACCATACCT CCTTTACCAC CAAGTTACGA
1321 GTGTTTGGTT AAGTTTTGTA TGTTGATGCA GCGTGTGAGT ATCTTAGACT CTTAGTGTCT
1381 CCAGCCCCAT ATTCTTTTAA AACATGGAGG ACTGATCACT ATCCATAACT CTTTTAACAA
1441 AACTACACAC AAGAAATACA CATTTTTCAT CTCACACACA GTTTTAGGTA TACTAATATT
1501 TAATGTAATT AAAGGTTTTC TTAGTTATCA TATTTTGGGA TATAATAAAA ACTGTATAGG
1561 TTGAACTTTT TATAGTGACT GGGCTCACTC CGAAGGGTCA CCTTGCCAGA AATCTCCGTA
1621 GGGATTTTTT AGCTAACCCA GTACCACCCC GCTGTCCCTG AGTATCGAAC TGGCGACCTC
1681 GGGTAATCGT GTGTGAGAAA CGTTCAGTAC TGCCGCTAGG CACCTGACGT TCTCAAAAAA
1741 ACTGTATAGG TTGAACTTTT TTTAATAACT AGGCTCACCC CGGAGATCAC CTCGCCAGAA
1801 ATCCCCGTAG ATATAATAAC CATATAGCCT CCAAAAGTGG AGCAATTTCT TTGAAACGCA
1861 TCTCATCCAT ATAGAGACCA ACATTAACCA TTATCACCAA TTCACTCTTT ATTTCCACCT
1921 AACCATTTAA AAGTCTATAT ATATATATAT ATATATATAT ATATATGTTA AAGGAGCTAA
1981 ATTAATCAAA AATGATAAAC ATCTAATATA TCCTATTCTC CTATATATAG ACACTCCCAC
2041 TAACTCTCAC AGACCCACAA CACTCACACC ATCATG
```

FIGURE 1A

Pis 63/GUS
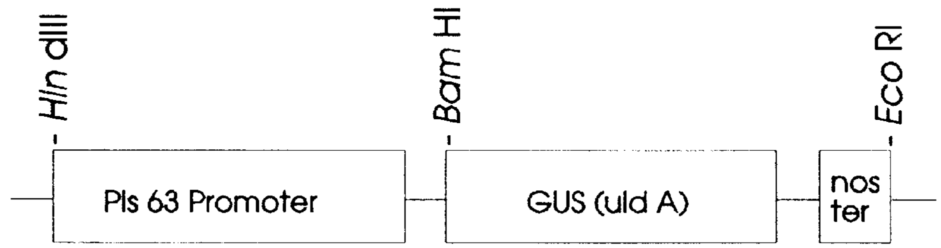
pBI 221
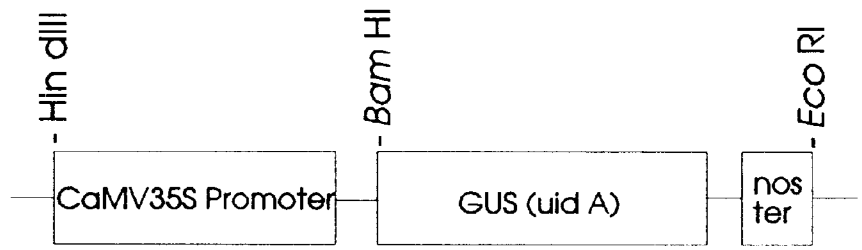
Promoterless/GUS
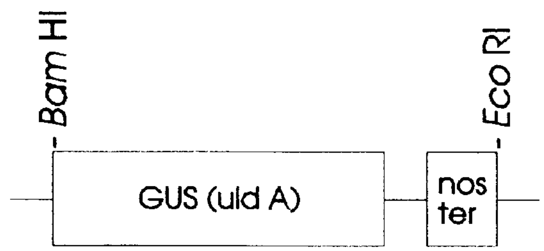
FIGURE 2

Pis 63 Promoter / GUS

Pis 63 Promoter / GUS

Promoterless / GUS

BRASSICA SP. GENE PROMOTER HIGHLY EXPRESSED DURING STIGMA DEVELOPMENT

The present invention relates to plant gene promoters. Specifically this invention relates to a gene promoter that directs high levels of transcription during pistil development, preferentially stigma development.

BACKGROUND OF THE INVENTION

The pistil is the reproductive organ of the angiosperm flower which harbours the female gametophyte (Esau K., *Plant Anatomy,* John Wiley, New York (1965)). In spite of its critical role in plant reproduction, relatively few genes have been identified which are predominantly expressed in pistils and most of the characterized genes function primarily within the transmitting tissue (Gasser C. S., Robinson-Beers K., *Plant Cell* 5:1231–1239 (1993)) or are associated with self-incompatibility (Nasrallah J. B., Nasrallah M. E., *Plant Cell* 5:1325–1335 (1993); Newbigin E., Anderson M. A., Clarke A. E., *Plant Cell* 5:1315–1324 (1993); Trick M., Heizmann P., *Int. Rev. Cytol* 140:485–524 (1992)).

In order to isolate additional genes which are important to pistil function and development, a *Brassica napus* flower cDNA library constructed in λgt10 was differentially screened as described previously (Robert L. S., Allard S., Franklin T. M., Trick M., *Mol. Gen. Genet* 242:209–216 (1994)). One cDNA clone Pis 63 represented a gene highly expressed in the pistil and was investigated further (Robert L. S., Allard S., Gerster J. L., Cass L., Simmonds J., et al., *Plant Mol. Biol.* 26:1217–1222 (1994)). Northern blot analyses showed that Pis 63 transcripts were found primarily in the stigmatic region and that they could be detected in stigmas throughout pistil development starting with low levels in 1–2 mm flower buds. Pis 63 transcripts were still present one week post anthesis, but were absent in the stigma dissected from a 4 cm silique.

In situ hybridization performed on median longitudinal sections of 3 mm developing flower buds showed that Pis 63 expression was limited to the stigmatic cells of the pistil. A $^{35}$S-labelled Pis 63 antisense ribo-probe hybridized strongly to the papillar cells of the stigma, whereas no differential hybridization was observed with the sense RNA probe. No hybridization was detected in the style or the ovary.

A limited number of genes have been shown to function primarily in the stigma and they include proteinase inhibitors from *Nicotiana alata* (Atkinson A. H., Heath R. L., Simpson R. J., Clarke A. E., Anderson M. A., *Plant Cell* 5:203–213 (1993)), chitinases from *Petunia hybrida* (Leung, D. W. M., *Phytochemistry* 31:1899–1900 (1992)) and genes involved in the sporophytic self-incompatibility system of Brassica (Goring D. R., Glavin T. L., Schafer U., Rothstein S. J., *Plant Cell* 5:531–539 (1993); Nasrallah J. B., Nasrallah M. E., *Plant Cell* 5:1325–1335 (1993); Robert L. S., Allard S., Franklin T. M., Trick M., *Mol. Gen. Genet* 242:209–216 (1994); Trick M., Heizmann P., *Int. Rev. Cytol* 140:485–524 (1992); and PCT application WO 94/25613.

The Brassica pistil is considered to have a dry stigma with the external surface of its papillar cells being covered by a protein pellicle (Mattson O., Knox R. B., Heslop-Harrison J., Heslop-Harrison Y., *Nature,* 247:298–300, 1974). Since the Pis 63 gene product may be secreted, it could form a constituent of the papillar protein pellicle and hence be involved in encouraging the germination of compatible pollen or discouraging pathogen infection. The relevance of the similarity between the Pis 63 protein and a protein expressed in cotton fibre remains to be elucidated. This cotton protein encoded by pCEK6 may play either a structural role, or a role in the biosynthesis or degradation of polysacharides within cotton fibre (John M. E., Crow L. J., *Proc. Natl. Acad. Sci* USA 89:5679–5773 (1992). It is possible that both these proteins serve similar functions as structural or defence proteins.

Accordingly, it is thus desirable to isolate the promoter region from a genomic clone corresponding to said cDNA clone, wherein said promoter region could be used to direct high levels of transcription to the stigma.

SUMMARY OF THE INVENTION

The present invention relates to plant gene promoters. Specifically this invention relates to a promoter that directs high levels of transcription in the stigma.

In one embodiment of the present invention there is provided a Brassica sp. gene promoter that directs high levels of transcription in the stigma.

The present invention is also directed to a chimeric gene construct comprising the Brassica gene promoter of the present invention and the coding sequence of a gene, for which stigma-directed expression is desired.

The present invention is further directed to a method of conferring stigma-directed expression of a gene in a plant, comprising:

- operatively linking a gene, for which stigma-directed expression is desired, with a Brassica sp. gene promoter of the present invention to produce a chimeric gene;
- introducing the chimeric gene into an appropriate vector; and
- introducing the vector into a plant capable of expressing the chimeric gene.

The present invention is further directed to transgenic plants containing a chimeric gene construct as described above.

BRIEF DESCRIPTION OF THE DRAWINGS

These and other features of the invention will become more apparent from the following description in which reference is made to the appended drawings wherein:

FIG. 1 is the nucleotide sequence of the 5' upstream region containing the promoter fragment of the *B. napus* stigma-expressed gene, which corresponds to SEQ ID NO: 1. The ATG start codon is underlined. This promoter fragment up to position 2073 was used with the GUS fusion construct.

FIG. 2 shows the construct of plasmids promoterless/GUS, pBI 221 and Pis 63/GUS.

FIG. 3 (C) show stigma bombarded with a promoterless/GUS construct. Arrow points to stigma.

DESCRIPTION OF PREFERRED EMBODIMENT

Figure 3A:
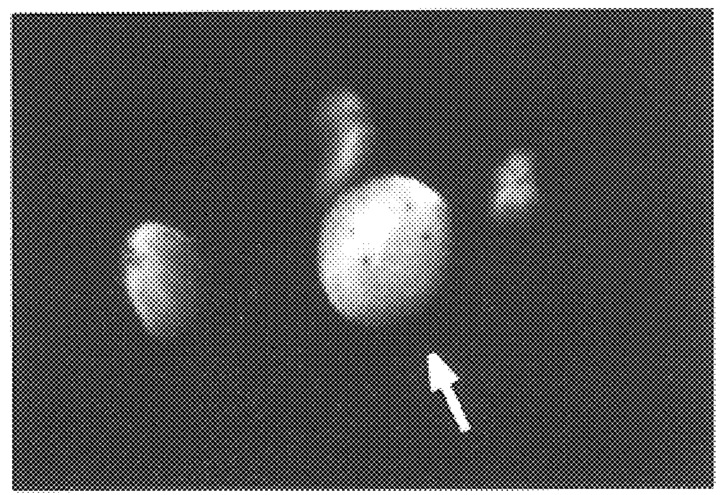
FIG. 3 (A & B) show staining for GUS activity of the Pis 63/GUS construct bombarded on the stigma of *B. napus* cv. Westar. Arrow points to stigma.

The present invention relates to plant gene promoters. Specifically this invention relates to a gene promoter that directs high levels of transcription in the stigma.

In the context of this disclosure, the tens "promoter" or "promoter region" refers to a sequence of DNA, usually upstream (5') to the coding sequence of a structural gene, which controls the expression of the coding region by providing the recognition for RNA polymerase and/or other factors required for transcription to start at the correct site.

The present invention is directed to a promoter which facilitates the spacial and temporal expression of a gene in the stigma. Specifically, the present invention is directed to a gene promoter isolated from Brassica sp.

One embodiment of the present invention is directed to a promoter isolated from *Brassica napus.* Sequences substantially homologous to Pis 63 have been detected in other species of Brassica (results not shown). Thus, the present invention is not limited to the promoter isolated from *Brassica napus,* but includes within its scope the corresponding promoter from other species of Brassica.

The present invention is further directed to a chimeric gene construct containing a gene of interest wherein said gene is operatively linked to the promoter of the present invention. Any gene can be used and manipulated according to the present invention to result in the stigma-directed expression of said gene.

The Pis 63 promoter could be used to direct the expression of genes to the stigma in an effort to inhibit pollination, fertilization and/or seed production. Female sterility could be achieved by fusing the Pis 63 promoter to genes whose products would disrupt the development of stigmatic cells. For example, the promoter of the present invention could be fused to a gene encoding the diphtheria toxin A chain (Thorsness M. K., Kandasamy M. K., Nasrallah M. E., Nasrallah J. B., *Dev. Biol.* 143:173–184 (1991[])) or the Barnase gene from *Bacillus amyloliquefaciens* (Goldman M. H. S., Golderg R. B., Mariani C., *EMBO. J.* 13:2976–2984 (1994)). The Pis 63 gene itself could be used. If this gene is critical to stigmatic cell development or pollination, for example, expressing an antisense version or a sense version (in this case the inhibition could occur by co-suppression) of this gene in the stigma could reduce the Pis 63 activity and result in female sterility. Female sterility may be desirable, for example, in the production of hybrid seeds or seedless fruits. The Pis 63 promoter could be also used to direct the expression of genes which would facilitate or modify pollination, fertilization and/or seed production. For example, the promoter of the present invention could be used to target the expression of genes which would alter the stigmatic composition to modify self-compatibility or self-incompatibility characteristics, or to reduce pathogen infection.

In the context of the present disclosure, the term "operatively linked" is meant to mean that the various components of the chimeric gene construct of the present invention are positioned so as to ensure the proper transcription, or transcription and translation of the desired sequence. For example, a chimeric gene could be constructed by replacing the coding region of the genomic clone Pis G363 with the complete or partial coding region of another gene in the sense or anti-sense orientation. A chimeric gene could also be constructed by replacing a specific promoter with the promoter of the present invention in such a way as to allow the proper transcription, or transcription and translation of a particular sequence in the stigma.

The chimeric gene construct of the present invention can further comprise a 3' untranslated region. A 3' untranslated region refers to that portion of a gene comprising a DNA segment that contains a polyadenylation signal and any other regulatory signals capable of effecting MRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the structural gene of the present construct can also be used.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be of a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase, uid A), or luminescence, such as luciferase are useful.

Also considered part of this invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Any plant species can be modified according to the present invention to include the chimeric gene construct to provide pistil-, specifically stigma-directed expression of a gene.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology,* Academy Press, New York VIII, pp. 421–463 (1988); and Grierson and Corey, *Plant Molecular Biology,* 2nd Ed. (1988). The present invention further includes a suitable vector comprising the chimeric gene construct.

When specific sequences are referred to in the present invention, it is understood that these sequences include within their scope sequences that are "substantially homologous" to said specific sequences. Sequences are "substantially homologous" when at least about 80%, preferably at least about 90% and most preferably at least about 95% of the nucleotides match over a defined length of the molecule. Sequences that are "substantially homologous" include any substitution, deletion, or addition within the sequence. DNA sequences that are substantially homologous can be identified in Southern hybridization experiments, for example under stringent hybridization conditions (see Maniatis et al., in Molecular Cloning (A Laboratory Manual), Cold Spring Harbor Laboratory (1982) p 387 to 389). Such substantially homologous sequences have been found in Brassica sp.

The specific sequences, referred to in the present invention, also include sequences which are "functionally equivalent" to said specific sequences. In the present invention functionally equivalent sequences refer to sequences which although not identical to the specific sequences provide the same or substantially the same function. Sequences that are functionally equivalent include any substitution, deletion or addition within the sequence. With reference to the present invention functionally equivalent sequences will also direct the expression of a gene to the pistil, preferentially to the stigma.

While this invention is described in detail with particular reference to preferred embodiments thereof, said embodiments are offered to illustrate but not limit the invention.

EXAMPLES

Example 1: Isolation of the *B. napus* Genomic Clone Containing a Stigma-Expressed Gene The spring *B. napus* cv. Westar genomic library was constructed in the vector λ DashII as recommended by the manufacturer (Stratagene). Genomic DNA was extracted from nuclei (Jofuku and Goldberg, 1988, in *Plant Molecular Biology:* a practical approach, 37–66), partially digested with Sau 3A and size fractionated (9–20 kb) as described in Unit 5.3-*Current Protocols in Molecular Biology* (1987). The genomic library (300,000 plaque forming units) was probed with the [$^{32}$P]oligolabelled Pis 63 cDNA clone (Robert et al., *Plant Mol. Biol.,* 26:1217–1222, 1994). A genomic clone, Pis G363, containing a sequence identical to the *B. napus* stigma-expressed gene Pis 63–2 was isolated and characterized.

A Bgl II fragment of approximately 7 Kb from Pis G363 containing the 5' upstream region of the Pis 63 gene was subcloned into pGEM 4Z (Promega) and used to generate the Pis 63 promoter fragment. The sequence of this promoter fragment is shown in FIG. 1 (SEQ ID NO: 1). The sequence of this promoter fragment as found in its native form, is as depicted in FIG. 1. For a reference, the initiation codon ATG from the Pis G363 genomic clone is also shown and underlined in FIG. 1. For the promoter-GUS fusion constructs, the promoter fragment used is that as shown in FIG. 1, up to the nucleotide position 2073, as shown by the arrow in FIG. 1. This promoter fragment (2073 bp) was obtained by the polymerase chain reaction (PCR) using the primer G 363-3, 5'-TTAGGATCCGATGGTGTGAGTGTTGTGGGT-3' (SEQ ID NO: 2) which is complementary to sequence −1 to −21 bp upstream of the translational start ATG in Pis G363 (and to which a Bam HI site was added) and the T7 promoter primer found in the pGEM 4Z plasmid.

Amplifications were performed in a 100 μl volume containing 1X Taq DNA polymerase buffer (Promega)/1.5 mM $MgCl_2$/0.2 mM dNTPs/250 ng of each primer/1 ng of the subcloned DNA. Following 5 min. at 95° C., 2.5 U of Taq polymerase was added and 35 cycles of 1 min. at 95° C., 1 min. at 55° C., 2 min. at 72° C. were performed and followed by a 10 min. extension at 72° C. The Pis 63 promoter/PCR fragment was identified by sequencing and then subcloned as a Bam HI/Hind III fragment upstream of the GUS gene of the vector pBI 221 (Clontech) replacing the CaMV 35S promoter to yield the Pis 63/GUS fusion construct (FIG. 2).

Example 2 Microprojectile Bombardment of the Stigma with Pis63/GUS

To verify that the 5' flanking sequence from the genomic clone Pis G363 contained the regulatory sequences required to confer expression in stigma cells, the Pis63/GUS fusion construct was introduced into *B. napus* cv. Westar flower cells via high-velocity microprojectile bombardment. The use of microprojectile bombardment as an effective transient assay system for floral promoters has been demonstrated previously (for example: Eyal Y., Curie C., McCormick S., *Plant Cell* 7:373–384 (1995); Hamilton D. A., Roy M., Rueda J., Sindhu R. K., Sandford J., Mascarenhas J. P., *Plant Mol. Biol.* 18:211–218 (1992); Lonsdale D. M., Allen R. L., Belostotsky D., Ghose T. K., Harvey A. J., Rogers H. J., Tebbutt S. J., Trick M., *Plant Cell Rep.* 15:154–158 (1995); Tebbutt S. J., Lonsdale D., M., *Sex Plant Reprod.* 8:242–246 (1995); Twell D., Klein T. M., Fromm M. E., McCormick S., *Plant Physiol.* 91:1270–1274(1989)). As a positive control experiment, the *B. napus* flower cells were separately bombarded with the vector pBI 221 (FIG. 2). This vector contains the GUS gene driven by the CaMV 35S promoter which is a promoter highly expressed in all plant organs. As a negative control, the flower cells were bombarded separately with a promoterless/GUS fusion construct (FIG. 2). This vector was constructed by subcloning the GUS coding region and nopaline synthase polyadenylation signal from the vector pRD420 (Datla R. S. S., Hammerlindl J. K., Panchuk B., Pelcher L. E., Keller W., Gene 211:383–384 (1992)) as a Bam HI/Eco RI fragment into pGEM 4Z (Promega).

The microprojectile bombardment was performed as follows. Sepals and petals were removed from floral buds (5 mm). The floral stalks with gynoecium and androecium were embedded individually in 3% low melting agarose containing Murashige and Skoog salts and 12% sucrose in 1.5 ml Eppendorf tubes so that the anthers and pistil remained exposed to the air. These explants were equilibrated in petri dishes for 3 h at 25° C. prior to gene delivery. The DNA (vectors pBI 221, promoterless/GUS or Pis63/GUS) was precipitated onto 1.6 μm diam. gold particles (BioRad) as follows. DNA (5 μg) was added to 50 μl aqueous gold suspension (60 μg/μl) and vortexed for a few seconds. 25 μl of $CaCl_2$ (2.5 M) was added and the mixture was vortexed. 5 μl of spermidine (0.1M) was also added and the mixture vortexed. The suspension was allowed to settle and the supernatant was removed. The gold particles were resuspended in 50 μl absolute ethanol and 0.5 μl aliquots of this suspension were loaded into the restriction capillary of the micro-targeting device (Sautter C., Waldner H., Neuhaus-Uri G., Galli A., Neuhaus G., Potrykus I., *Biotechnol.* 9:1080–1084 (1991)). The stigmatic area of each explant was centred into the gold flight-path and the gold suspension was delivered by pressurized nitrogen at 1000 psi. Following bombardment, the explants were cultured overnight at 25° C. in the dark before being assayed histologically for GUS activity.

GUS activity was localized by histochemical staining essentially as described previously (Jefferson R. A., *Plant Mol. Biol. Rep.* 5:387–405 (1987)). Bombarded explants were submerged overnight at 37° C. in Eppendorf tubes containing a solution of 100 mM sodium phosphate pH 7.0, 20 mM EDTA, 0.1% Triton X-100, 1.0 mM potassium ferrocyanide, 1.0 mM potassium ferricyanide and 1.0 mM X-gluc (5-bromo-4-chloro-3-indolyl-μ-D-glucuronic acid).

Figure 3B:
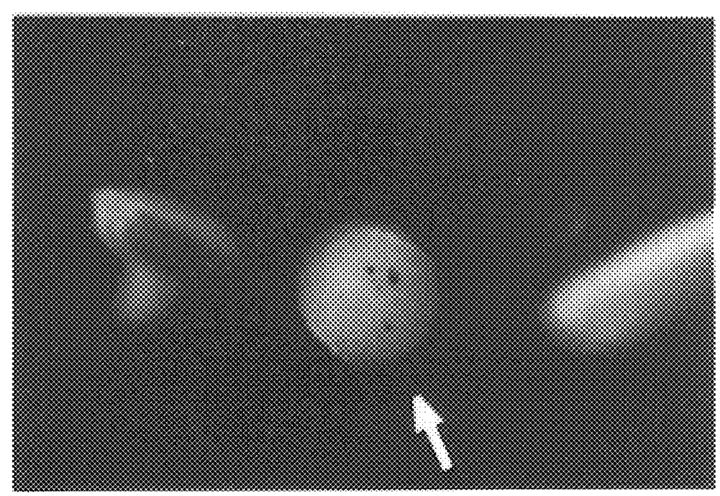
Figure 3C:
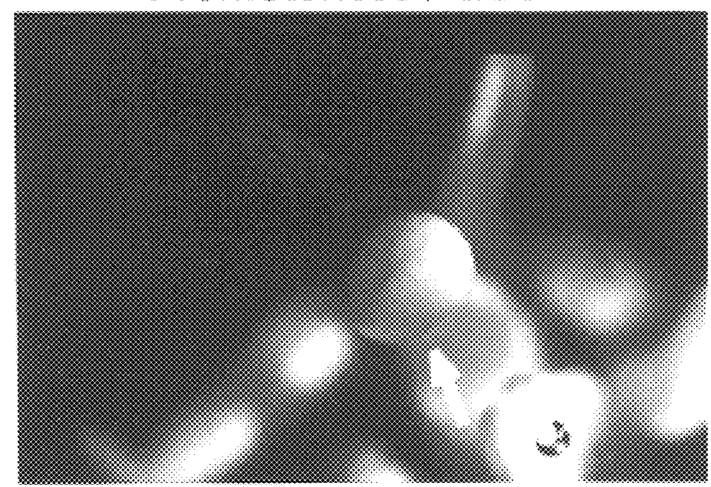

GUS activity (blue spots) was consistently observed in the stigma of flowers bombarded with the fusion vector Pis 63/GUS (FIG. 3A, 3B), whereas no GUS activity was detected in flower tissues bombarded with the promoterless/GUS construct (FIG. 3C). As expected, all the tissues (for example, stigma, style, anthers) which received the pBI 221 vector containing the GUS gene fused to the constitutive CaMV 35S promoter showed GUS activity (results not shown). This indicates that the 5' flanking region from the genomic clone Pis G363 used as a promoter fragment in the Pis 63/GUS construct contains the necessary cis acting regulatory elements required for stigma expression.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

The embodiments of the invention in which an exclusive property or privilege is claimed are defined as follows:

1. An isolated and purified Brassica sp. promoter, which directs expression in stigma wherein said promoter has a nucleotidle sequence which is at least 80% homologous to SEQ ID NO:1.

2. The promoter according to claim 1, wherein the Brassica sp. is *Brassica napus.*

3. The promoter according to claim 1, wherein said promoter has a nucleotide sequence of SEQ ID NO:1.

4. A chimeric gene construct comprising a Brassica sp. promoter and the coding sequence of a gene, wherein said promoter directs transcription of the gene in stigma and wherein said promoter has a nucleotide sequence which is at least 80% homologous to SEQ ID NO:1.

5. The chimeric gene construct according to claim 4, wherein the Brassica sp. is *Brassica napus.*

6. The chimeric gene construct according to claim 4, wherein said promoter has a nucleotide sequence of SEQ ID NO:1.

7. A vector comprising the chimeric gene construct of claim 4.

8. The vector according to claim 7, wherein the Brassica sp. is *Brassica napus.*

9. The vector according to claim 7, wherein said promoter has a nucleotide sequence of SEQ ID NO:1.

10. A method of conferring stigma-directed expression on a gene in a plant, comprising:

operatively linking a gene, for which stigma-directed expression is desired, with a Brassica sp. gene promoter, which directs expression in the stigma and wherein the promoter has a nucleotide sequence at least 80% homologous to SEQ ID NO: 1, to produce a chimeric gene;

introducing the chimeric gene into an appropriate vector; and introducing the vector into a plant capable of expressing the chimeric gene.

11. The method according to claim 10, wherein the Brassica sp. is *Brassica napus.*

12. The method according to claim 10, wherein said promoter has a nucleotide sequence of SEQ ID NO:1.

13. A transgenic plant containing the chimeric gene construct of claim 4.

14. The transgenic plant according to claim 13, wherein the Brassica sp. is *Brassica napus.*

15. The transgenic plant according to claim 14, wherein said promoter has a nucleotide sequence of SEQ ID NO:1.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
(A) LENGTH: 2076 base pairs
(B) TYPE: nucleic acid
(C) STRANDEDNESS: double
(D) TOPOLOGY: linear (xi) SEQUENCE DESCRIPTION: SEQ ID NO: 1:

```
GGGGATCTAT CTTAGATATT GTTTGAAAAG AGAGTACCAA CTCTCCCATA CTCAAAGTCA     60

CAGAAGTCAA ATGTTGTTTG AAATAATTAT AGCATTTGTT TGTTTTAGTT AAAAGTTTGA    120

AAAACTACGA ACGATTTATG GATCATCATT CATCACGCAT ATTGTTAATG TGAGAACCAG    180

ACCAATAGTT TCTTAAGTAT TGAATATACA AAAAACATTT GATAAACAAA TCTTTCGCTT    240

TGGAAAAATA TAGGGTGGGT AATATTTTGT ATAATCTAAG CGGCTTGTTC ATTTGTAATC    300

ATGGATTTTA ATGTTTTTGA TGACTTTGTT TGTGGATGTG CAACTGCATA TTTTTAGTTT    360

TTTTTGTTTG TTAATTGTGT TGTGATCCTT AATCCTAATT ATGAAACACA CAAGTATGAC    420

TGATAAGAGT TAGTAAGCAT TCGGTGGTCA AGATATTTAG TGGCTAGCGA CCTACCCCTA    480

ATTTATTTAT TTATTTTAAC TAATCTTTAT TTGATCGTTC ATTATGTCAA CAAACTTTCT    540

TCTTCTCTAA AGTACGTGAA ATTACTACTA CATTTTAATA CTGCAATTGA AGTAAGTAGT    600

ACGGTTTTCA TCTCTTAAAT GCATGGAAAC AAACACTAAT ACGTAGCAAA ATTGAGAGAA    660

CATATACTAT GCTTCGCACC GGATTTTATT AGAGCATTTG ACACACTAAA GTCCCACATG    720

GTTACCAGCA GGGCCTGCCC TGAGATTTAG AGGGAGGTGG TTTTTAAAAA AAATTCCGTT    780

AAAAATTTTT TTTGGTAAAT TTGGAGGTCT AAAAAAAAAT TTTAAAAGTT TTTTCCTATG    840

TAATTTTTTC CAAAATTTTT AGAGGTCTAA GCCTAATATT TCGTTAGGCT TTAAGCAGGA    900

CCGGCCCTGG TTACCATATG TATAATACAT ACACAAAACA CAATTGTGTT GTCGTTTTTA    960

GTACTTTGTG TCCGTTTCAT TGTATATGAC GTACGTAACC ATTCAAAACC TAATTAAATA   1020

TGGTGATCCC CTAATTGATC ACATTCTAAG CTCTGGTAAA CTTCTCATGG CATACTCTTT   1080

TGATTTCGTA AACCCTTTCT CAAAAAGCTA TTTTCGTATT AATTTGGTAA GAATTATTTT   1140

CCTGGTCCAT GTAGGTTTTG TATGTTTTTT TTTTTGATAA CTCTGGTATC TGGGCAGCCA   1200

CATTCCCAAC TATCCATTCG AAAGGGGTCC AGCGCCCCGG GATGTTAAAT CCTGTTGTGG   1260

CCAAGGCTCG AACCCGGGTA GCGGCAGTAC AACCATACCT CCTTTACCAC CAAGTTACGA   1320

GTGTTTGGTT AAGTTTTGTA TGTTGATGCA GCGTGTGAGT ATCTTAGACT CTTAGTGTCT   1380

CCAGCCCCAT ATTCTTTTAA AACATGGAGG ACTGATCACT ATCCATAACT CTTTTAACAA   1440

AACTACACAC AAGAAATACA CATTTTTCAT CTCACACACA GTTTTAGGTA TACTAATATT   1500
```

-continued

```
TAATGTAATT AAAGGTTTTC TTAGTTATCA TATTTTGGGA TATAATAAAA ACTGTATAGG   1560

TTGAACTTTT TATAGTGACT GGGCTCACTC CGAAGGGTCA CCTTGCCAGA AATCTCCGTA   1620

GGGATTTTTT AGCTAACCCA GTACCACCCC GCTGTCCCTG AGTATCGAAC TGGCGACCTC   1680

GGGTAATCGT GTGTGAGAAA CGTTCAGTAC TGCCGCTAGG CACCTGACGT TCTCAAAAAA   1740

ACTGTATAGG TTGAACTTTT TTTAATAACT AGGCTCACCC CGGAGATCAC CTCGCCAGAA   1800

ATCCCCGTAG ATATAATAAC CATATAGCCT CCAAAAGTGG AGCAATTTCT TTGAAACGCA   1860

TCTCATCCAT ATAGAGACCA ACATTAACCA TTATCACCAA TTCACTCTTT ATTTCCACCT   1920

AACCATTTAA AAGTCTATAT ATATATATAT ATATATATAT ATATATGTTA AAGGAGCTAA   1980

ATTAATCAAA AATGATAAAC ATCTAATATA TCCTATTCTC CTATATATAG ACACTCCCAC   2040

TAACTCTCAC AGACCCACAA CACTCACACC ATCATG                             2076


(2) INFORMATION FOR SEQ ID NO: 2:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear

    (xi) SEQUENCE DESCRIPTION: SEQ ID NO: 2:

TTAGGATCCG ATGGTGTGAG TGTTGTGGGT                                      30
```